US005105803A

United States Patent [19]

Burton

[11] Patent Number: 5,105,803

[45] Date of Patent: Apr. 21, 1992

[54] GRAVITY TRACTION DEVICE WITH A BASE SUPPORT

[75] Inventor: Charles V. Burton, Excelsior, Minn.

[73] Assignee: Spinal Designs International, Inc., Minneapolis, Minn.

[21] Appl. No.: 607,745

[22] Filed: Oct. 29, 1990

Related U.S. Application Data

[63] Continuation of Ser. No. 489,712, Feb. 28, 1990, abandoned, which is a continuation of Ser. No. 301,176, Jan. 24, 1989, abandoned.

[51] Int. Cl.[5] .......................... A61H 1/02; A61F 5/02

[52] U.S. Cl. ........................................ 602/36; 602/19; 482/143

[58] Field of Search ....................... 128/75, 68, 69, 71; 272/134, 140, 144

[56] References Cited

U.S. PATENT DOCUMENTS

| | | | |
|---|---|---|---|
| 3,103,357 | 9/1963 | Berne | 272/134 |
| 3,353,532 | 11/1967 | Ellis | 128/75 |
| 4,030,489 | 6/1977 | Buckner | 128/75 |
| 4,205,665 | 6/1980 | Burton | 128/68 |
| 4,269,279 | 5/1981 | Burton et al. | 128/75 |
| 4,396,012 | 8/1983 | Cobiski | 128/75 |
| 4,422,452 | 12/1983 | Burton | 128/75 |
| 4,515,152 | 5/1985 | Teeter | 128/75 |
| 4,569,340 | 2/1986 | Burton | 128/75 |
| 4,583,533 | 4/1986 | Goodley et al. | 128/75 |
| 4,715,362 | 12/1987 | Scott | 120/75 |
| 4,746,116 | 5/1988 | Inada | 272/144 |

FOREIGN PATENT DOCUMENTS

| | | | |
|---|---|---|---|
| 1243327 | 6/1967 | Fed. Rep. of Germany | 128/75 |
| 3104832 | 1/1983 | Fed. Rep. of Germany | 128/75 |
| 3420858 | 12/1985 | Fed. Rep. of Germany | 128/75 |
| 0797664 | 1/1981 | U.S.S.R. | 128/75 |
| 8001540 | 8/1980 | World Int. Prop. O. | 128/75 |

*Primary Examiner*—Edgar S. Burr
*Assistant Examiner*—Moshe I. Cohen
*Attorney, Agent, or Firm*—Merchant, Gould, Smith, Edell, Welter & Schmidt

[57] ABSTRACT

A device and method for transferring stress from a lumbar spine to a rib cage includes an abdomen surrounding member and first and second support bars cooperatively connected to the sides of the abdomen surrounding member. The abdomen surrounding member is secured in an engaging position and a base support is adapted and configured to receive the first and second support bars. The device may also provide the additon feature to gain physically beneficial exercise in conjunction with gravity traction.

20 Claims, 2 Drawing Sheets

GRAVITY TRACTION DEVICE WITH A BASE SUPPORT

This is a continuation of application Ser. No. 07/489,712, filed Feb. 28, 1990, which is a continuation of Ser. No. 07/301,176, filed Jan. 24, 1989, which was abandoned upon the filing hereof.

FIELD OF THE INVENTION

This invention refers generally to a apparatus for transferring weight stress and loading from the lumbar spine to the rib cage of an individual. More specifically, this invention relates to utilizing the force of gravity to promote normal nutrition and healing of the lumbar spine and its components. This device utilizes a support which encompasses the torso as well as an adjustable base support, whereby the apparatus is portable. The device provides an apparatus for exercise relative to the disc tissue of the lumbar spine. The art by which this invention was developed reflects over a decade of medical clinical research and testing.

BACKGROUND OF THE INVENTION

Back pain is a common and significant mallady afflicting large numbers of people and virtually every country of the world. The wide spread nature of the problem has been highlighted in numerous articles printed in both medical and news periodicals. Illustrative are articles entitled Bare-bones Facts About Your Aching Back from the December, 1980 issue of Readers Digest and the cover story from the July 14, 1980 issue of Time magazine.

Axial traction has been shown to be effective in treating certain types of low back ailments, preventing back ailments and to produce and sustain low back health. Such traction has been found to be an effective means of realigning improperly aligned or displaced vertebral elements as well as their associated invertebral discs and soft tissues. Such traction has also been shown to reduce herniated contained intervertebral discs. Further, such traction has also been shown in muscle and ligament injury or insult to reduce spasm and inflammation, enhance blood flow and to promote optional healing. Certain circumstances have, however, long presented obstacles to the effective application of controlled traction to the lumbar area. These circumstances include the significant amount of force which must be applied, the lack of a location at which the axially directed force can be applied, and the position of the person during which the axial force is being applied.

In 1971, the applicant provided for the construction of an apparatus to support a person, such person having one of a number of conditions such as a protruded lumbar disc, in a vertical position wherein the torso of the person was suspended by a chest harness encircling the rib cage. As a result of the research, the applicant has proven scientifically and conclusively that the rib cage can serve as an optimum site of fixation and does serve well this purpose. He determined that, in order for the harness to function most effectively, it must, at its lower end, be tightened beneath the rib cage so that, as axial force is applied to the harness, the rib cage will not slide therethrough.

After continued research, the applicant invented an improved gravity traction vest. Prior to this time, the tightening of a lower most belt of the gravity vest was accomplished exclusively by providing a belt having a sufficient number of locking points whereby the belt could be tightened so that it was within the perimeter of the rib cage regardless of the size of the person being treated. Applicant invented the new improved gravity traction vest that provided means whereby axial fixation could be efficiently accomplished, yet wherein the treatment is not rendered uncomfortable. Applicant filed a patent application Ser. No. 299,679 on Sep. 8, 1981 for the improved gravity traction vest. This application was allowed on Aug. 17, 1983 and has been granted U.S. Pat. No. 4,422,452.

While the improved second generation gravity traction vest provided improvement over the original gravity traction vest, there remained a number of problems associated with its use. These problems included the need to tighten a number of cinctures to secure the vest to the person, the rough surfaces of the cinctures being felt through the vest by the person. While there was an improved locking of the vest to the person due to the cushion insert, it was desirable to provide for still more positive locking. The need to provide comfort to the person has always been a goal which each generation has tried to accomplish. The goal was to provide a vest which allowed the person to accept therapy and not cause discomfort. While there has been improvement in this area, there has been the need for still more improvement.

It is these problems in the prior art that a third generation gravity traction vest was developed. It provides for a torso surrounding member being constructed of the rigid material, a simple and effective means for securing the vest to the person and a flanged under portion that protrudes inwardly toward the person for engagement below both the lowest rib and the inverted U-shaped area of the rib cage. U.S. Pat. No. 4,569,340 was issued on Feb. 11, 1986 on such a vest.

While the inventor's vests have been utilized for many persons and have proved quite successful, all of the vests to date have required overhead support of the vest. This is a drawback in that such devices are large and cumbersome and are best utilized in a hospital or clinic setting.

U.S. Pat. No. 3,353,532 issued to L. C. Ellis describes a traction apparatus wherein support is provided to a patient by side members and does not utilize a vest which encircles the patient's body. However, such a device has not proven to the practical in that there is no means for gradual force applied to the spine. Still further, the side members appear to work by a simple compression from just underneath the armpits of the patient to just above the waist of the patient.

The successful prior art devices have tended to be vests and have accordingly encircled the torso of the person using the device. Although the vests have been employed successfully, one of the inherent drawbacks of a vest is that a large portion of the torso is encircled and breathing can be somewhat restricted as the tightly cinched vest covers the rib cage. Further, because the torso is encircled, there is a greater heat build up for the person. Further, because of the total device design, the person is somewhat restricted from accomplishing movement of the body such that beneficial tissue exercise can not be accomplished. In addition, the overall devices of previous apparatus have tended to be large, relatively expensive and not easily transportable.

The present invention addresses the problems associated with the prior art devices and provides for an effective means of transferring stress from a lumbar spine to a rib cage of a person wherein no overhead support is necessary to support the device. The device has flexible pivot points which aid in accomplishing exercise and at the same time transfer stress. The device is a lower cost unit which can be used in the home, while travelling, in conference rooms, health clubs and many other places outside of a medical setting.

SUMMARY OF THE INVENTION

The present invention is a device for transferring stress from a lumbar spine to the torso of the body, which is above an abdomen, of a person. The device includes an abdomen surrounding member for substantially surrounding the abdomen of the person. The abdomen surrounding member has a top edge. The abdomen surrounding member has a first side and a second side. Each of the sides have a section for engaging and supporting the person below the rib cage. A first support bar is cooperatively connected to and extends outward from the first side and a second support bar is cooperatively connected to and extends outward from the second side. A means for securing the abdomen surrounding member in an engaging position is also provided. A base support is adapted and configured to receive said first and second support bars. The base support is positioned substantially below the top edge of the abdomen surrounding member. In a preferred embodiment, the abdomen surrounding member is cooperatively connected to the base support by flexible coupling members for rotational movement. Also, a spring-damper device allows for vertical movement.

DETAILED DESCRIPTION OF THE PREFERRED EMBODIMENT

Figure 1:
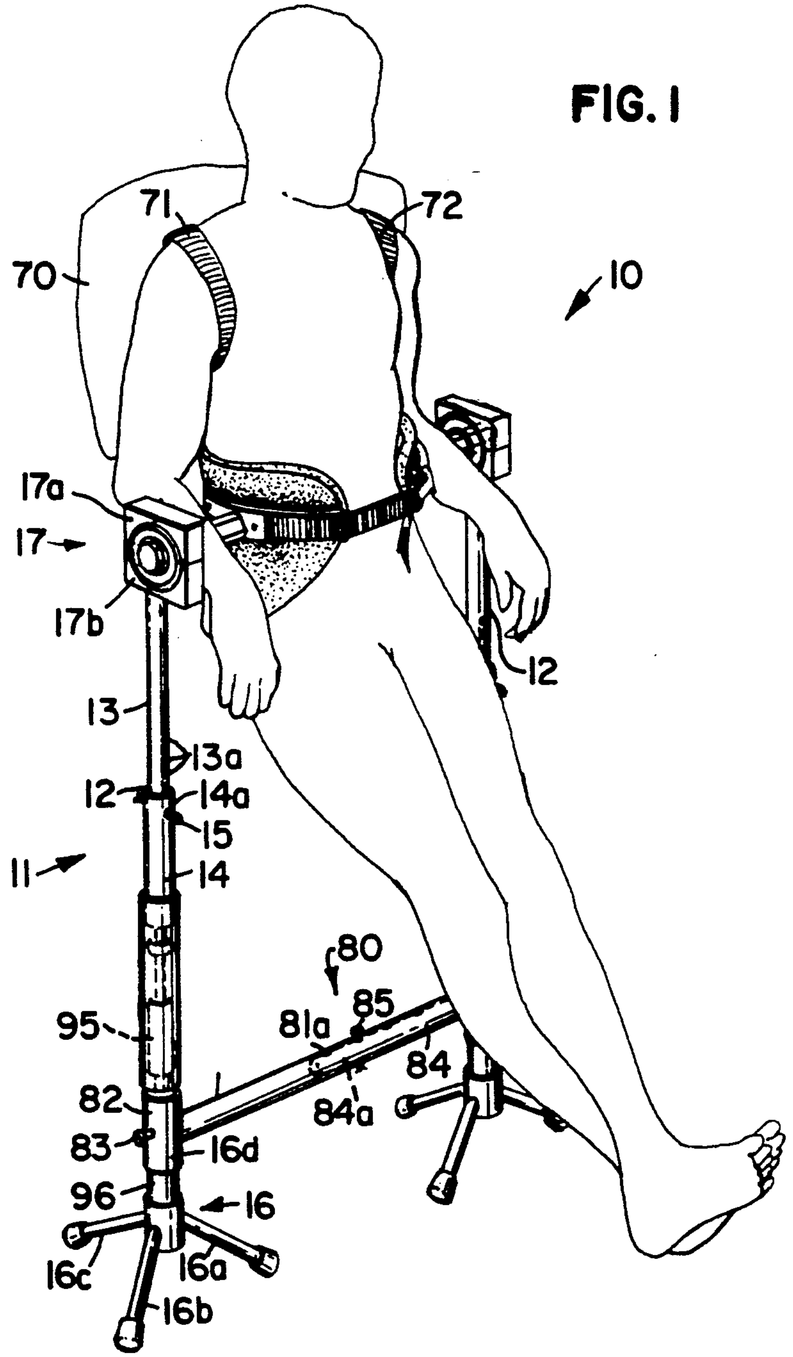
FIG. 1 is a perspective view showing one embodiment of the present invention.

Referring to the drawings, wherein like numbers represent parts throughout the several views, there is generally disclosed at 10 in FIG. 1 a gravity traction apparatus. The gravity traction apparatus 10 includes generally a support structure, generally disclosed at 11 and a gravity traction belt member, generally disclosed at 31 in FIG. 2. The support structure 11, as shown in FIG. 1, includes two stands 12. The stands 12 are telescoping so that their overall height may be adjusted, depending upon the height of the person using the device. A first post 13 has a diameter slightly less than the inner opening in the second post 14 so that it may slide up and down in the second post 14. The first post 13 has a plurality of spaced apart holes 13*a* which extend through the post 13. The post 14 has one set of holes 14*a* which are in alignment with one of the sets of holes 13*a*. A pin 15 is inserted through the hole 14*a* and then through one of the sets of the holes 13*a* and finally out the other side of the post 14, whereby the overall height of the stand 12 is fixed. Cooperatively connected to the second end of the post 14 is a spring damper device 95. The device 95 is a shock absorber which will allow vertical movement. The other end of the device 95 is cooperatively connected to a third post 96. The stand 12 has a base 16 which comprises three legs 16*a*, 16*b* and 16*c*, cooperatively connected to a sleeve 16*d*. The third post 96 is placed inside of the sleeve 16*d*. The post 96 may be secured by means of a friction fit or with the assistance of a set screw. At the top end of the first post 13, a cradle 17 is cooperatively connected. The cradle 17 may be connected to the post 13 by any appropriate means such as welding. A cradle 17 is connected to both of the posts 13. However, in FIG. 2, only one cradle is shown for illustrative purposes only. The cradle 17 has an outer housing assembly 17*a* which surrounds and is cooperatively connected to a TORSILASTIC spring 17*b*. The TORSILASTIC spring 17*b* may be of a suitable type such as that supplied by the BF Goodrich Company of Akron, Ohio. The TORSILASTIC spring will allow for rotational movement and provides a flexible rotatable coupling. The TORSILASTIC spring 17*b* has an inner opening sized and configured to match with the size and configuration of the support bar 63. The support bar is placed inside of the TORSILASTIC spring 17*b* when in use, as shown in FIG. 1. The TORSILASTIC spring is an integral unit consisting of an inner metal shaft surrounded by molded rubber cylinder with an outer shell of high strength metal alloy. The cylinder is strongly bonded to both the inner shaft and the outer shells forming a compact, lightweight unit. When the support bar 63 is inserted in the opening, spring action occurs when one of the middle components is rotated (caused by the rotation of the support bar 63) in relationship to the other. The rubber resists this deformation and returns to the original position when the force is released. Thereby, a rocking or rotational motion may be imparted by the wearer. While the cradles 17 are shown attached to the support arms, it is understood that they could be incorporated into the stand. Overall, the stand 12 may be constructed with any suitable material such as chromium plated steel tubing sufficient to provide support for the person using the gravity traction apparatus 10. In addition, other suitable configurations may be used to support the belt member 31. A spacer bar assembly, generally designated at 80, cooperatively connects the bottom portions of the two stands 12. The spacer bar assembly 80 includes a first bar 81 cooperatively connected by suitable means, such as welding, to a sleeve 82. The sleeve 82 has a bore such that the third post 96 slides inside of the bore. A set screw 83 goes through the sleeve 82 and is tightened on the post 96 in order to secure the sleeve to the post. The bar 81 has a plurality of holes 81*a* on both its top surface and bottom surface. A second bar 84 is slidable within the inner bore of the first bar 81 and also has a plurality of holes 84*a* in its top surface and bottom surface. The second bar 84 is slid into the first bar 81 until the holes 81*a* and 84*a* align so as to yield the required width between the two stands 12. A pin 85 is then inserted through holes 81*a* and 84*a* to hold the bar assembly 80 at its desired width. A sleeve (not shown) is cooperatively connected to the end of the bar 84 so that it similarly may go over the post stand 12. In FIG. 1, this is obscured by the legs of the person using the present invention. However, it is similar in construction to the sleeve 82.

Figure 3:
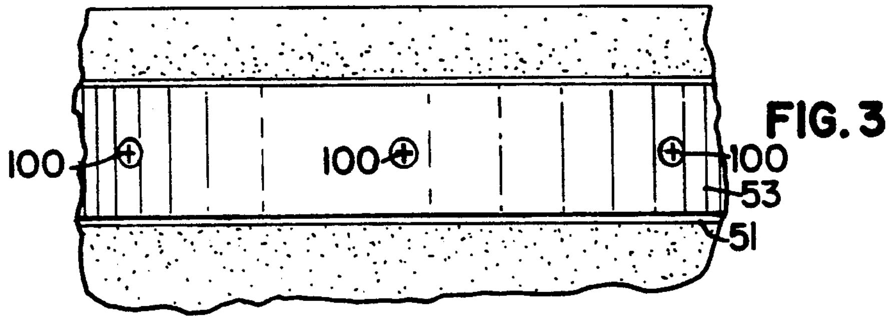
FIG. 3 is a back elevational view of a portion of the belt member shown in FIG. 1.
Figure 2:
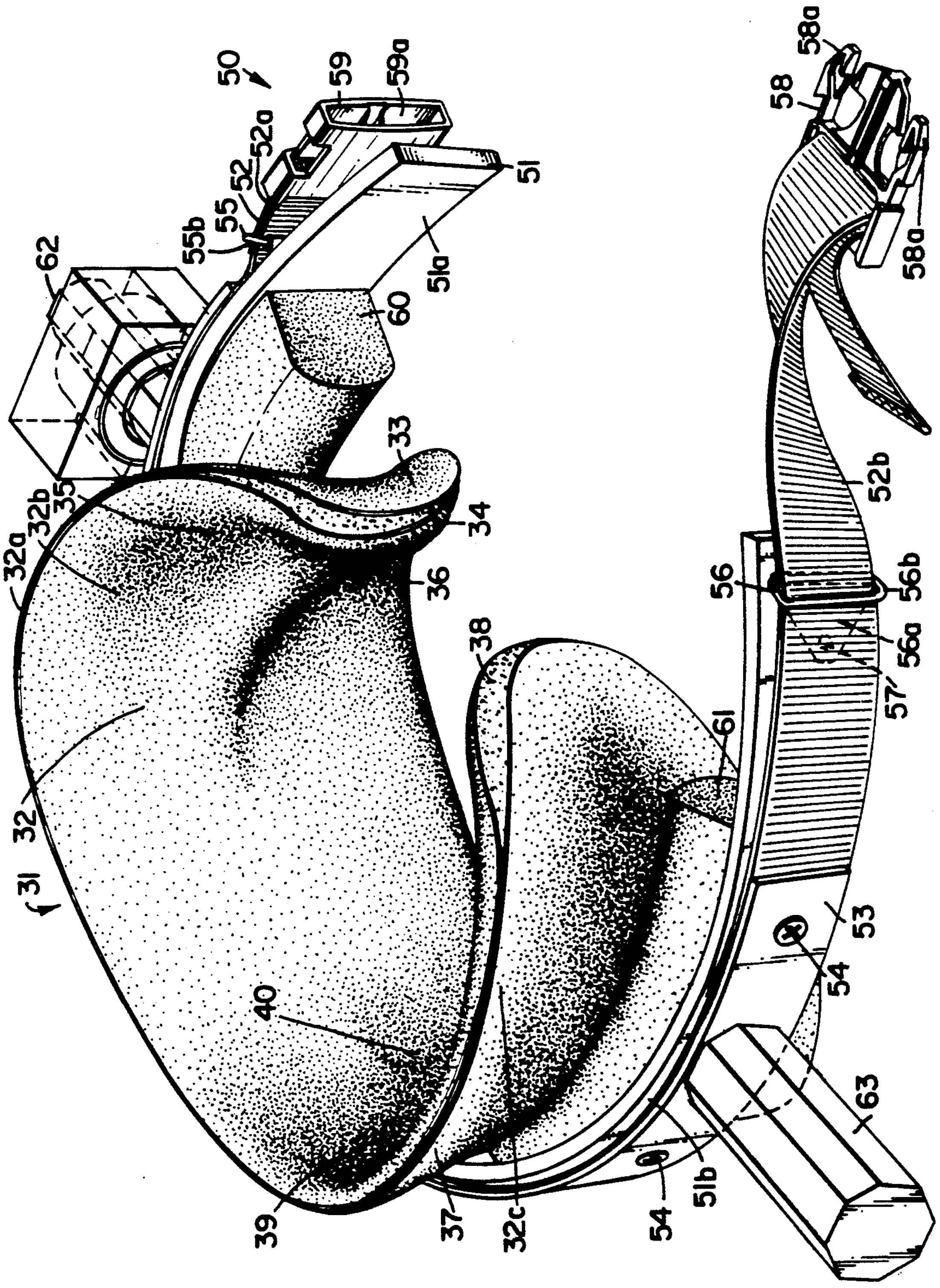
FIG. 2 is a perspective view of the belt member shown in FIG. 1.

The gravity traction belt member 31 is best seen in FIGS. 2 and 3. The belt member 31 includes an abdomen surrounding member 32 for substantially surrounding the abdomen of the person. The abdomen surrounding member 32 has a top edge 32*a*. Further, the abdomen surrounding member 32 has a first side 32*b* and a second side 32*c*. As shown in FIG. 2, the first side 32*b* is a mirror image of the second side 32*c*. Further, it can be seen that the sides 32*b* and 32*c* are one continuous piece, although it is understood that the invention could also include an abdomen surrounding member wherein the sides were not of a unitary construction. The first side 32*b* has an outside surface 33 which may be of any suitable material such as a polymeric material, such as a rigid formable plastic of suitable thickness and design to support and conform to the rib cage of the person, i.e., ¼ inch A.B.S. plastic. A pad 34, preferably of a semi-rigid polymeric material, such as a high density closed cell foam rubber, is placed between the outer surface 33 and the inner surface 35. It is understood that any cushioning material, such as an air bladder or free flowing foam pellets, may also be utilized. The inner surface 35 is typically constructed of a soil resistant and cleanable semi-rigid polymeric material, which will allow the foam material 34 to ultimately comply with the person's profile. The semi-rigid polymer, such as a foam 34 is inserted in the appropriate places, as shown in FIG. 2, to form a support which fits comfortably under the rib cage of the wearer. The portion of the side 32*b* which would fit immediately under the rib cage is the protrusion 36 and this protrusion 36 would ultimately provide the support under the rib cage of the person.

The second side 32*c* has an outside surface 37, similar to and continuous with surface 33. A pad 38, similar to pad 24, preferably of a semi-rigid polymeric material, such as a high density closed cell foam rubber, is placed between the outer surface 37 and the inner surface 39, similar to and continuous with inner surface 35. An optional removeable cover may enclose the abdomen surrounding member 31. The cover would be a cleanable soil resistant material, such as a nylon cloth. While a three core structure is shown, other suitable configurations may be utilized. The three core structure may be suitably bonded together by an appropriate adhesive. The semi-rigid polymer, such as a foam 38 is inserted in the appropriate places, as shown in FIG. 2, to form a support which fits comfortably under the rib cage of the wearer. The portion of the side 32*c* which would fit immediately under the rib cage is the protrusion 40 and this protrusion 40, along with protrusion 36, would ultimately provide the support under the rib cage of the person. While the above-noted construction is preferred, it is understood that other suitable shapes may be utilized. This may include shapes where there is no protrusions 36 and 40 and the person is supported by the top edge 32*a* underneath the person's rib cage. Applicant has found that a protruding foam pad or other formable material in the middle of the sides 32*b* and 32*c* provides for more comfortable support. The teachings of applicant's prior patents with respect to support may be utilized in developing alternate embodiments of a suitable support.

A belt assembly, generally designated at 50, is cooperatively connected to the abdomen surrounding member 32. A plastic member 51, having the general C-shape, has an inside surface 51*a* and an outside surface 51*b*. A strap 52 such as a webbed strap, is placed around the outside surface 51*b* of the plastic member 51. A metal strap 53, preferably made of tempered spring steel, is constructed to be positioned around the strap 52. The plastic member 51, strap 52 and metal support strap 53 are then cooperatively connected by suitable means, such as screws 54. While not shown, there are also two screws 54 on the belt assembly 50 which is proximate the first side 32*b*, similar to that shown proximate the second side 32*c*.

The web strap 52 is further connected, at its first end 52*a*, to the plastic member 51 by a clip 55 which is secured to the plastic member 51 by suitable means, such as screws or rivets. The second end 52*b* of the strap 52 is similarly further connected to the plastic member 51 by means of a clip 56 which is attached to the plastic member 51 by suitable means such as a rivet or screw 57. The clips 55 and 56 both have a base member and ring which comprise the clip. As shown in FIG. 2, the clip 56 has a The strap passes through the ring member 56*b* at its second end and through ring member 55*b* at its first end. A fastener is provided for connecting the strap 52 and thereby the entire belt assembly 50. The fastener includes a suitable tongue member 58 cooperatively connected to the second end 52*b* of the strap 52 and a buckle 59 cooperatively connected to the first end 52*a* of the strap 52. While any suitable fastener may be utilized, the fastener shown is preferable in that it provides for a quick release as will be more fully described hereafter. The tongue member 58 has deformable fingers 58*a* which are compressed and slide into the receiving hole 59*a* of the buckle 59. Once inserted, the fingers 58*a* spring back and extend through the locking holes 59*b*.

A wedge shaped foam insert 60 is cooperatively connected to the inside surface 51*a* to the belt assembly 50 proximate the first side 32*b* and a similar wedge shaped foam insert 61 is cooperatively connected to the inside surface 51*a* to the belt assembly 50 proximate the second side 32*c*. The inserts 60 and 61 may be cooperatively connected by suitable means, such as bonding with an adhesive.

A first support bar 62, constructed of metal, is cooperatively connected to the metal strap 53 by suitable means such as welding. In a preferred embodiment, the support bar 62 is an octagonal rod. The rod 62 is cooperatively connected to the metal strap 53 proximate the first side 32*b*. A second support bar 63 is similarly cooperatively connected to the metal strap 53 proximate the second side 32*c*. The bars 62 and 63 are positioned along the metal strap 53 such that when the belt assembly 50 is closed and the belt member 31 is tightly surrounding the person wearing it, the bars are in a general axial alignment, that is approximately 180° apart. The support bars 82 and 83 have a configuration to match the opening in the TORSILASTIC spring in the cradle 17.

The belt assembly 50 is then cooperatively connected to the belt member 31 by any suitable means. One manner of connecting the belt assembly 50 is shown in FIG. 3, wherein three screws pass through the belt assembly 50 and pass through to the outside surface 33 of the belt member 31. These three screws 100 are equally spaced along the back side of the belt member 31. Alternately, threaded studs could be molded on the plastic member 51 and the studs would extend through holes in metal strap 53 with nuts then being used to secure the assembly.

It is understood that the overall size of the belt member 31 will vary depending upon the size of the person utilizing the belt member 31.

In operation, the standing person using the gravity traction apparatus 10 will place the stands 12 at a distance such that the cradles 17, which are adapted and configured to receive the support bars 62 and 63, are positioned around the support bars 62 and 63 and the metal spacer bar assembly 80 is positioned and affixed. The stands 12 may be set up at any convenience location, but it is preferred that the stands be placed proximate a wall for back support, as will be more fully discussed hereafter. The person then places the belt member 31 around his abdomen such that the protrusions 36 and 40 are positioned underneath his rib cage. The opening between the first side 32*b* and second side 32*c* can be increased by simply flexing the sides 32*b* and 32*c* away from each other. The belt member 31 is of such a construction that this flexing is allowable. The length of the strap 52 is then adjusted such that when the tongue 58 is inserted into the buckle 59, the belt assembly 50 is tight around the person's abdomen. The belt assembly 51 is inherently resilient and tends to stay in a position wherein the ends are spaced apart from each other at a distance greater than what would be normal in a closed position. By inserting the tongue 58 into the buckle 59, the belt assembly 50 is snugged tight, bringing the ends closer together thereby embracing the abdomen of the person and supporting the person below the lower rim of the person's rib cage. In doing so, the inserts 60 and 61 may be compressed. The use of the inserts 60 and 61 allow the belt member 31 to have a tight fit around a number of persons having a different circumference around their abdomen.

The overall height of the floor mounted stands 12 needs to be adjusted based on the height of the person using the apparatus and also on the method of sue of the apparatus. After the person has the belt member 31 in place around his abdomen, he may simply position himself proximate the cradles 17 and then insert the supports arms 62 and 63 into the cradles 17. The octagonal shape allows the person to preset an original position. It is understood that gravity will tend to rotate the wearer to an upright position if the arms are not inserted so that the wearer is vertical. The TORSILASTIC spring will resist this, but typically would not be enough to retain the wearer at an angle. The person then moves his legs out from immediately between the stands 12 to in front of the stands, thereby removing support from the feet. The movement of the feet effects the weight transfer and may be achieved by having the person move his feet away from an underbody support position, or by lifting his feet or by moving the person's feet away from a vertical axis. In doing so, the stress from the lumbar spine is transferred to the rib cage. The person's weight is transferred from the person's feet to the stands 12 through the belt member 51, partially or fully dependent upon the position of the person's feet, either in a partial or no support fully extended position. The person's arms may use the support bars 62 and 63 as armrests while in use. It is understood that separate arm rests may be incorporated to increase the person's comfort. Another alternative would be to adjust the height of the stands 12 higher such that a stool is used to allow the person using the apparatus to be above the cradles 17 and then step off the foot stool, thereby having his feet suspended above the ground but still directly between the stands 12.

As previously indicated, it is preferable that the apparatus 10 be adjacent a wall. When in such a position, the person using the apparatus 10 may strap a pillow 70 onto his back by means of straps 71 and 72, which are cooperatively connected to the pillow 70, and lean against the wall for support. Additionally, a separate back support board may be attached to the back of the support member to provide suitable back support, similar to the function of the pillow/wall combination.

A combination of the spring dampening device 95 and the TORSILASTIC spring in the cradles 17 allow for the wearer to obtain beneficial exercise while at the same time transferring stress and loading from the lower spine to the rib cage. The wearer can shift his weight up and down in a jumping motion to provide for vertical motion. The spring dampening device 95 dampens any such movement and returns the apparatus back to its original position. This up and down motion provides exercise relative to the disc tissue of the lumbar spine. Still further, the wearer may rock forward and backward. The TORSILASTIC spring 17 will ultimately restrict the forward motion and then cause the wearer to go back to an original upright position. This also promotes exercise of the disc tissue of the lumbar spine.

It is also appreciated that the apparatus may include only one of these exercise devices as opposed to both of the exercise devices. Still further, it is understood that other ways of providing exercise may be utilized. One such method would be to not use a shock absorber device, but instead having the bars 62 and 63 slightly flexible which would allow for up and down motion and thereby exercise of the disc tissue.

Still further, it is appreciated that the exercise component should be supplied by many other suitable devices, such as a motor driven apparatus or using an overhead support harness having springs in the overhead support harness.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as present herein All alternative modifications and variations of the present invention which follow in the spirit and broad scope of the appended claims are included.

I claim:

1. A floor supported, non-overhead device for transferring stress from a lumbar spine to a rib cage of a person, the device comprising:

(a) an abdomen surrounding member for substantially surrounding the abdomen of the person, the abdomen surrounding member having a top edge, a first side and a second side, each of said sides of said abdomen surrounding member having a section for engaging and supporting the person below the rib cage, said first side operatively connected to said second side at the sides' rear portion and in a spaced relationship at the sides' front portion;

(b) a first support bar cooperatively connected to and extending outward from said first side;

(c) a second support bar cooperatively connected to and extending outward from said second side;

(d) means for securing said abdomen surrounding member in an engaging position, said securing means overlying the spaced relationship at the sides' front portion; and (e) a floor supported base configured to receive said first and second support bars.

2. The device of claim 1, wherein said base support is positioned substantially below the top edge of the abdomen surrounding member.

3. The device of claim 1, wherein said base support comprises a cradle cooperatively connected to an upright post.

4. The device of claim 3, wherein said cradle further comprises a first cradle and first post and a second cradle and second post, said first post cooperatively connected to said second post by a spacer bar assembly.

5. The device of claim 1 wherein said securing means comprises:

(a) a member surrounding said abdomen surrounding member;

(b) a flexible strap positioned around said member;

(c) a resilient support strap; and (d) means for cooperatively connecting said member, flexible strap and resilient support strap.

6. The device of claim 5, further comprising a foam cushion cooperatively connected to said member and positioned between said member and said abdomen surrounding member.

7. The device of claim 4, wherein said support bars are octagonal in cross-section.

8. The device of claim 7, wherein said first and second cradles each have an opening configured to receive and secure said support bars at an angle orientation desired by the person using the device.

9. The device of claim 1, further comprising means for permitting controlled rotational movement of said support bars, wherein the person may exercise while also transferring stress.

10. The device of claim 1, further comprising means for allowing controlled vertical movement of the person, wherein the person may exercise while also transferring stress.

11. A floor supported, non-overhead device for supporting a person proximate a rib cage, for transferring stress from a lumbar spine to the rib cage, the device for use with a base support, the device comprising:

(a) an abdomen surrounding member for substantially surrounding the abdomen of the person, the abdomen surrounding member having a top edge, a first side and a second side, each of said sides of said abdomen surrounding member having a section for engaging and supporting the person below the rib cage, said first side operatively connected to said second side at the sides' rear portion and in a spaced relationship at the sides' front portion;

(b) a first support bar cooperatively connected to nd extending outward from said first side;

(c) a second support bar cooperatively connected to nd extending outward from said second side;

(d) means for securing said abdomen surrounding member in an engaging position; and (e) the support bars configured to be supported by a base support which is positioned below the top edge of the abdomen surrounding member.

12. A floor support, non-overhead device for providing gravity traction to the lumbar spine of a patient starting from a standing position which comprises:

(a) an abdomen surrounding member for substantially surrounding the abdomen of the person, the abdomen surrounding member having a top edge, a first side and a second side, each of said sides of said abdomen surrounding member having a section for engaging and support the person below the rib cage, said first side operatively connected to said second side at the sides' rear portion and in a spaced relationship at the sides' front portion;

(b) a first support bar cooperatively connected to and extending outward from said first side;

(c) a second support bar cooperatively connected to and extending outward from said second side;

(d) means for securing said abdomen surrounding member is an engaging position, said securing means overlying the spaced relationship at the sides' front portion; and (e) a base support configured to receive said first and second support bars said base supports configured to operatively support said support bars underneath the person and not above the person.

13. A method of providing gravity traction to the lumbar spine of a person without use of an overhead harness or support which method comprises the steps of:

(a) embracing the abdomen of a person with support means for engaging and supporting the person below the lower rim of the person's rib cage and securing the support means such that the support means and securing means completely encircle the person's abdomen;

(b) engaging the support means into a floor mounted base; and (c) transferring a portion of the person's weight from the person's feet to the base through the support means.

14. The method of claim 13 in which the weight transfer is achieved by having the person move his or her feet away from an underbody support position.

15. The method of claim 13, wherein the weight transfer is achieved by the person lifting his or her feet.

16. The method of claim 13, wherein the weight transfer is achieved by moving the person's feet away from a vertical axis.

17. A method of providing gravity traction to the lumbar spine of a person and also exercise of the spine which method comprises the steps of:

(a) embracing the abdomen of a person with a support means for engaging and supporting the person below the lower rim of the person's rib cage said base supports configured to operatively support said support bars underneath the person and not above the person;

(b) the person engaging a support means to transfer a portion of the person's weight from the lumbar spine to the support member the support means including generally upright members; and (c) moving the person by varying the length of the upright support members, while also transferring stress, to allow for exercise of the lumbar spine.

18. The method of claim 17, further comprising moving the person rotationally.

19. A floor mounted non-overhead device for transferring stress from a lumbar spine to a rib cage of a person, and also allowing exercising, the device comprising:

(a) a support means for engaging and supporting the person below the lower rim of the person's rib cage;

(b) means for engaging, by a person, the support means, wherein there is a transfer of stress from the person's lumbar spine to the support member the support means including generally upright members; and (c) means for allowing movement of the device, and thereby the person also, by varying the length of the upright support members wherein the person may exercise the lumbar spine as well as transfer stress simultaneously.

20. The device of claim 19, wherein the movement means permits rotational movement of the person.

* * * * *